United States Patent [19]
Carlson

[11] Patent Number: 5,375,465
[45] Date of Patent: Dec. 27, 1994

[54] METHOD FOR GAS/LIQUID WELL PROFILING

[75] Inventor: Norman R. Carlson, Houston, Tex.

[73] Assignee: Royal Wireline, Inc., Mercedes, Tex.

[21] Appl. No.: 48,378

[22] Filed: Apr. 15, 1993

[51] Int. Cl.$^5$ .................... E21B 47/00; E21B 49/10
[52] U.S. Cl. .................................................. 73/155
[58] Field of Search .................. 436/25, 29; 73/151, 73/155, 154

[56] References Cited

U.S. PATENT DOCUMENTS

| | | | |
|---|---|---|---|
| 4,573,354 | 3/1986 | Voorhees et al. | 436/25 |
| 4,574,118 | 3/1986 | Demaoson et al. | 436/29 |
| 4,947,682 | 8/1990 | Anderson et al. | 436/29 |

OTHER PUBLICATIONS

T. O. Allen and A. P. Roberts, "Well Completions Workover and Stimulation", *Production Operations,* vol. II.

N. R. Carlson, "Profiling Gas–Water Flows in Deviated Pipe" (1991).

N. R. Carlson and R. M. McKinley, *Production Logging APplications and Reservoir Managment* (1992).

*Primary Examiner*—Amalia L. Santiago
*Attorney, Agent, or Firm*—Sue Z. Shaper

[57] ABSTRACT

A method for profiling of a gas and liquid producing wells comprising compiling calibration data from measuring instruments within non-in situ test equipment, valuing downhole gas and liquid density, determining average values for downhole instrument measurements and predicting, utilizing the above information, a percent of total gas flow and a percent of total liquid flow at a downhole depth.

13 Claims, 10 Drawing Sheets

METHOD FOR GAS/LIQUID WELL PROFILING

FIELD OF INVENTION

This invention relates to a method for profiling production in a fluid producing well, and more particularly, to gas/liquid well profiling.

BACKGROUND OF THE INVENTION

Frequently "gas wells" produce over several zones. These zones may be separated by tens of feet or by a thousand or more feet. In fact, a half dozen or more production zones may exist for a given well.

The production output of gas and liquid at the surface, in units such as standard cubic feet per day or barrels per day, should be known for each well. Owners, however, frequently also want to know the gas/liquid well profile". This "gas/liquid well profile" indicates the fractional contribution of gas and/or liquid contributed by each production interval. The information is helpful, for instance, in determining whether to open a similar production interval at a given level in a subsequent or adjacent well, or in determining whether to work-over an existing well at certain production levels.

In general, intervals that produce primarily water are not desirable. Intervals that produce the highest percentage of the gas are of the most interest to the owner.

The "gas wells" to which this invention particularly relates produce combined gas and liquid. The liquid is expected to be predominately water or predominately oil. Lower portions of these wells may produce gas percolating through a column of stagnant water. Such a possibility should be taken into account by accurate and sensitive methods for profiling gas wells.

Reasonably accurate and sensitive "quantitative" methods for single phase well profiling are known in the industry. A single phase well produces only gas, only oil, or only water.

Suggestions for improving methods for single phase profiling where gas is produced by percolation through stagnant water, a special case of single phase production, have also been taught. An example of such is discussed below.

"Quantitative" methods for oil/water well profiling are also known in the industry. These methods are discussed below.

"Qualitative" methods are presently being utilized in the industry for profiling combined gas/liquid producing wells. The drawback of the "qualitative" approach is that it lacks the degree of discrimination desired by owners to effectively evaluate completions and manage reservoirs. There is a need, therefore, for sensitive and accurate "quantitative" methods for profiling combined gas/liquid producing wells.

It is believed that the direction that the industry is taking to "quantitatively" solve the problem of gas/liquid well profiling is to develop precise analytical models. The present invention, in contrast to the precise analytical approach, teaches a "quantitative" interpretive method for combined gas/liquid well profiling. The method avoids developing sophisticated analytical models. Rather, it teaches the use of non-in situ calibration data in combination with an interpretive scheme. The results of the method correlate unexpectedly well with the results of the best "qualitative" methods.

To review the prior art in more detail, Thomas O. Allen and Alan P. Roberts summarize and teach, in Vol. II of *Production Operations*, "Well Completions Workover and Stimulation", the current art of known instruments and methods for single phase and multi-phase well profiling. As pointed out by Allen and Roberts, when dealing with single phase production, or with dual phase combined production of oil and water, certain assumptions and simplifications can be made in regard to downhole conditions. Given readings of a downhole density measuring instrument, a downhole flow rate measuring instrument and proper "in situ" calibration, these assumptions and simplifications permit a "quantitative" analytical solution for profiling single phase production and dual phase oil/water production.

Figure 1:
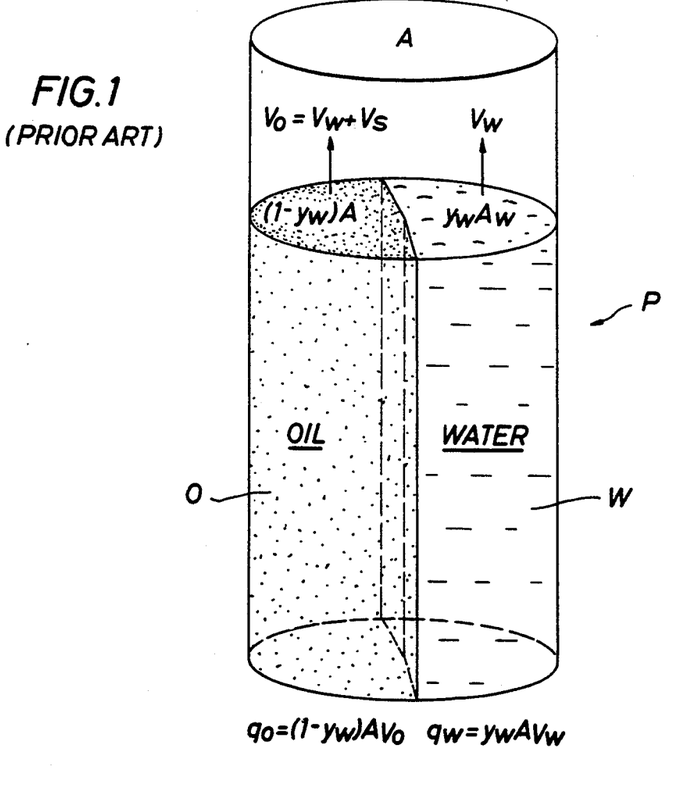
FIG. 1 indicates a segment of pipe illustrating dual phase production of oil and water.

FIG. 1 helps to illustrate the analytic art of oil/water well profiling. Noted upon FIG. 1 are the relationships among flow rate, q; water hold-up, y; and velocity, v. Illustrated therein is a volume of fluid in a pipe P, having a cross-sectional area A, wherein a portion of the fluid comprises water W and a portion of the fluid comprises oil O. The term "water cut" refers to the fraction of water in the total flow stream moving past a particular depth in the well bore in a given time period. Water cut, thus, equals $q_w/q_t$, the flow rate of water divided by total fluid flow rate. "Water holdup", $y_w$ (sometimes referred to herein as $H_w$), represents the fraction of water in a total volume of fluid at a particular level. Assuming that one has a value for the downhole density of the oil, $\rho_0$, and water, $\rho_w$, such as from measurements of the fluid densities with the well shut in, and that the apparent fluid density $\rho_t$ can be determined by a density measuring instrument at various depths, water holdup, $y_w$, can be calculated at various levels as:

$$y_w = \frac{\rho_t - \rho_0}{\rho_w - \rho_0}$$

Slippage velocity, $v_s$, is the difference between the oil stream velocity, $v_0$, and the water stream velocity, $v_w$, $v_s = v_0 - v_w$. Slippage velocity can be determined empirically for oil/water production by knowing the difference in density between oil and water and the water holdup.

FIG. 1 relates the flow rates of water and oil to water holdup and slippage velocity. With these factors, and with a measurement of the rate of the total flow, $q_t$, by an appropriate flow meter instrument, the oil flow rate $q_0$ and water flow rate $q_w$ moving by a particular level can be quantitatively determined by the following formulas:

$$q_0 = (1 - y_w)(q_t + v_s A y_w)$$

$$q_w = y_w[q_t - A v_s(1 - y_w)]$$

Water cut can be determined at that level from the equation water cut equals $q_w/q_t$. Utilizing such equations, zones contributing water can be "quantitatively" identified.

It is tacitly recognized by Allen and Roberts that the above analytic "quantitative" method for profiling the combined production of oil and water does not work per se for the combined production of gas and liquid. One reason for this is that the density of gas downhole, as contrasted with oil, is clearly a function of the pressure and temperature and should vary with depth. Slippage velocity can not be reliably determined empirically. Computing the downhole slip velocity should require knowing the densities of the fluids at that point. To recite what was stated above, to solve this problem it is believed that the industry is experimenting with a complex simulation model that takes into account dynamic downhole conditions and solves, analytically, for slip velocity in gas/liquid producing wells.

What Allen and Roberts do specifically make reference to, when treating multiphase fluid movement that includes gas, is the common practice in the art today of utilizing "qualitative" techniques. For "gas" wells, Allen and Roberts teach that .downhole moving temperature logs and moving density logs are "read" by experts who predict, based upon their experience and expertise, entry of gas and/or liquid at certain production levels. An example is offered of an evaluation of a gas well completion using such "qualitative" methods.

In the 1991 publication "Profiling Gas-Water Flows in Deviated Pipe", N. R. Carlson has shown, for combined air/water flow in test equipment (air at ambient temperature and atmospheric pressure and water selected from the municipal water supply), that measured flow meter instrument readings (in spinner revolutions per second, or counts per second) vary with total fluid flow rate and "water cut." Carlson also shows how density instrument readings (presented as water holdup readings) vary with the variation in total flow rate and water cut. Carlson demonstrates the accuracy of an interpretive method when applied to surface data for interpolating from known data for the instruments to estimated values for water cut and total flow rate corresponding to new measurements.

Carlson does not teach, in the 1991 article, a protocol for adapting the interpretive method to downhole measurements in order to perform gas/liquid well profiling. The article does not teach or suggest how to adapt the scheme to profiling when one expects to encounter non-linear variations in temperature, pressure, density and slip velocity for combined gas and liquid production.

In a mid-1992 article, *Production Logging Applications in Reservoir Management,* Norman R. Carlson and R. M. McKinley discuss an example of profiling gas flow through stagnant water. This comprises a special case of single phase production and suggests a benefit from the use of calibration data (as opposed to linear assumptions) when dealing with flow meter readings in gas production. Linear assumptions may be too inaccurate, for the special case of gas percolating through stagnant water. Typically, in single phase production, the readings of a flow meter are analyzed linearly: e.g., the revolutions per second (RPS) of the flow meter spinner above an interval minus the RPS of the spinner below the interval, divided by the RPS of the flow meter above all production levels, is taken to yield an approximation of the fractional contribution by the interval of the fluid being produced. The 1992 article shows that calibrating the downhole readings with a previously non in-situ generated non-linear RPS-to-gas-flow-rate curve for water cut=0 appears to yield profiles that correlate more closely with predictions based upon a moving temperature log.

Proposing a more sensitive and accurate method for predicting gas contributed by intervals where the gas percolates through stagnant water does not solve the dynamic interaction problems involved in quantitatively profiling combined production of gas and liquid. Only a single instrument, for instance, is needed to profile single phase production, including the percolating gas problem. Therefore, the 1992 article does not teach or suggest a sensitive and accurate "quantitative" method for profiling combined gas/liquid production.

SUMMARY OF THE INVENTION

The present invention discloses a technique for quantitative gas/liquid profiling of combined production wells, which technique correlates unexpectedly well with accepted "qualitative" interpretations and appears to offer a significant improvement in sensitivity and accuracy. Non-in situ calibration data are compiled for a fluid flow rate and a density measuring instrument. For the generation of such data, the instruments are placed within test equipment and liquid flow rates and gas flow rates are controllably varied. In the preferred embodiment, the test equipment comprises flow loop test equipment. In contrast to the direction believed being taken by the industry today, the non-in situ generated calibration data, together with a downhole gas and liquid density value, are used in a simplified scheme to interpret average measured downhole readings to profile the well.

The actual downhole readings are comprised of average values for a set of stationary measurements from two instruments taken over a period of time at each of a plurality of downhole depths. Preferably the averages are taken over at least an eight minute period of time. Such averages, interpreted by means of the calibration data and density values, permit a prediction of a percent of total gas flow and a percent of total liquid flow at a downhole depth.

The fluid density measurements are preferably converted to the variable "water holdup" for the calibration phase and the measurement phase. The preferred embodiment utilizes a diverting flow meter as a flow measuring instrument and a focused density tool as a density measuring instrument. In the preferred embodiment, readings are taken below, between and above all production intervals.

According to the preferred embodiment, in calibrating the instruments a first set of calibration curves are generated wherein the Y axis comprises values for a function of fluid flow rate, such as the spinner rate in revolutions per second or counts per second (CPS), and the X axis comprises values for total fluid flow rate. Each curve in this set represents a curve of values for a particular "water cut". A second set of calibration curves is generated wherein the Y axis comprises values for a function of fluid density, such as "water holdup" and the X axis comprises various values of "water cut". Each curve in this second set relates to a different total fluid flow rate. (The terms "water holdup" and "water cut" are used herein as defined terms of art, recognizing that the liquid in question actually may be "water" or may be oil, and is likely to be either predominantly water or predominately oil.)

In the preferred embodiment, given an average downhole measured value of a function of fluid flow rate, such as an average spinner CPS value, a line defined by such value can be drawn across the first set of calibration curves. The intersection of this line with each curve generates points defining a first solution curve. The solution curve is plotted on an interpretation graph, having X and Y axes comprised of values for water cut and total flow rate. A value of a function of averaged measured fluid density, such as "water holdup" (itself computed using values determined for downhole gas density and downhole liquid density), defines a line which can be drawn across the second set of calibration curves. The intersection of that line with the second set of curves generates points defining a second solution curve, which can be plotted on the above mentioned interpretation graph. The intersection of the first and second solution curves comprises a solution point. This point is taken as an indication of the total flow rate and water cut at the measured depth. The total flow rate and water cut can be converted to a gas flow rate and a liquid flow rate by suitable multiplication and subtraction.

More particularly, having gone through the above computations, the gas flow rate computed for a depth, divided by the gas flow rate computed for a depth above all producing levels (referred to as an uppermost normalizing depth), offers a predicted percent of gas flow for the depth. The liquid flow rate for a depth, divided by the liquid flow rate computed for the uppermost normalizing depth, offers a predicted percent of liquid flow for that depth.

In the preferred embodiment a running downhole temperature log and downhole density log may be read "qualitatively" to indicate when it appears that gas is percolating through stagnant water. The measured average instrument values, interpreted in light of the calibration data and the known output of the well, also may be used to detect situations that are consistent only with a stagnant water hypothesis. In such cases, resort is made to percolating gas calibration data.

BRIEF DESCRIPTION OF THE DRAWINGS

FIGS. 2 relate to measuring instruments.

FIGS. 4 illustrate a first and second set of calibration data curves. In particular.

DESCRIPTION OF THE PREFERRED EMBODIMENTS

In a well that produces both gas and liquid, a well profile indicates the production rates of the two fluids from each interval of interest. Such a profile may be important for raising the gas or oil production, reducing the water production and characterizing and managing the reservoir.

Generation of the flow profile typically utilizes flowmeter measurements which are a function of the total flow rate and density measurements which are a function of the "water cut" (e.g. the flow rate of liquid expressed as a fraction of the total flow rate). In view of the definition of "water cut" the arithmetic product of the total fluid flow rate and the "water cut" is the flow rate of the liquid. Subtraction of the liquid flow rate from the total fluid flow rate yields the flow rate of gas.

Figure 2A:
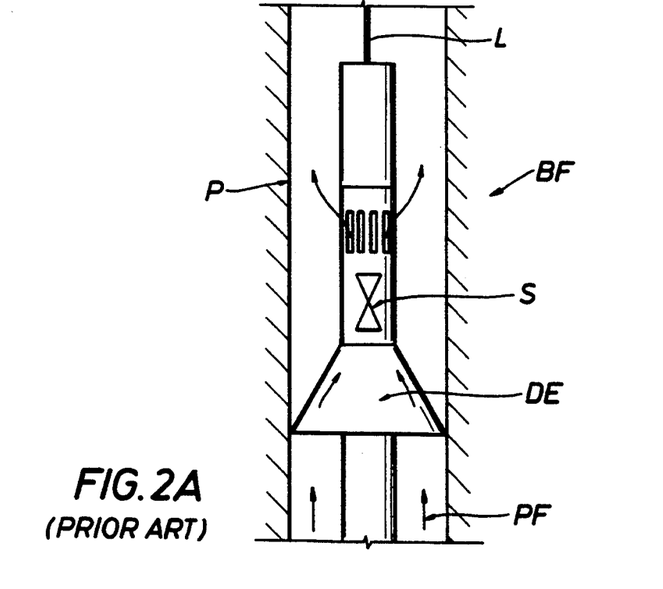
FIG. 2A illustrates a basket diverting flow meter.

The preferred embodiment of this invention discloses profiling gas/liquid flows in combined production wells utilizing a diverting flowmeter instrument, such as a basket flowmeter BF, in combination with a non-diverting, focused density tool, as the measuring instruments. The diverting flowmeter, as shown in FIG. 2A, includes a diverting element DE that opens up to meet the inside wall of a pipe P (in cased-hole production, or the surface of a borehole in open-hole production). The diverting element DE funnels the combined gas/liquid flow, or production flow PF, into a narrow channel inside the tool where the flow rotates a spinner S. The flow then is discharged to the wellbore. With the flowmeter stationary, the rotation rate of the spinner in revolutions per second (RPS) or counts per second (CPS) is measured and recorded.

Figures 2B, 2C:
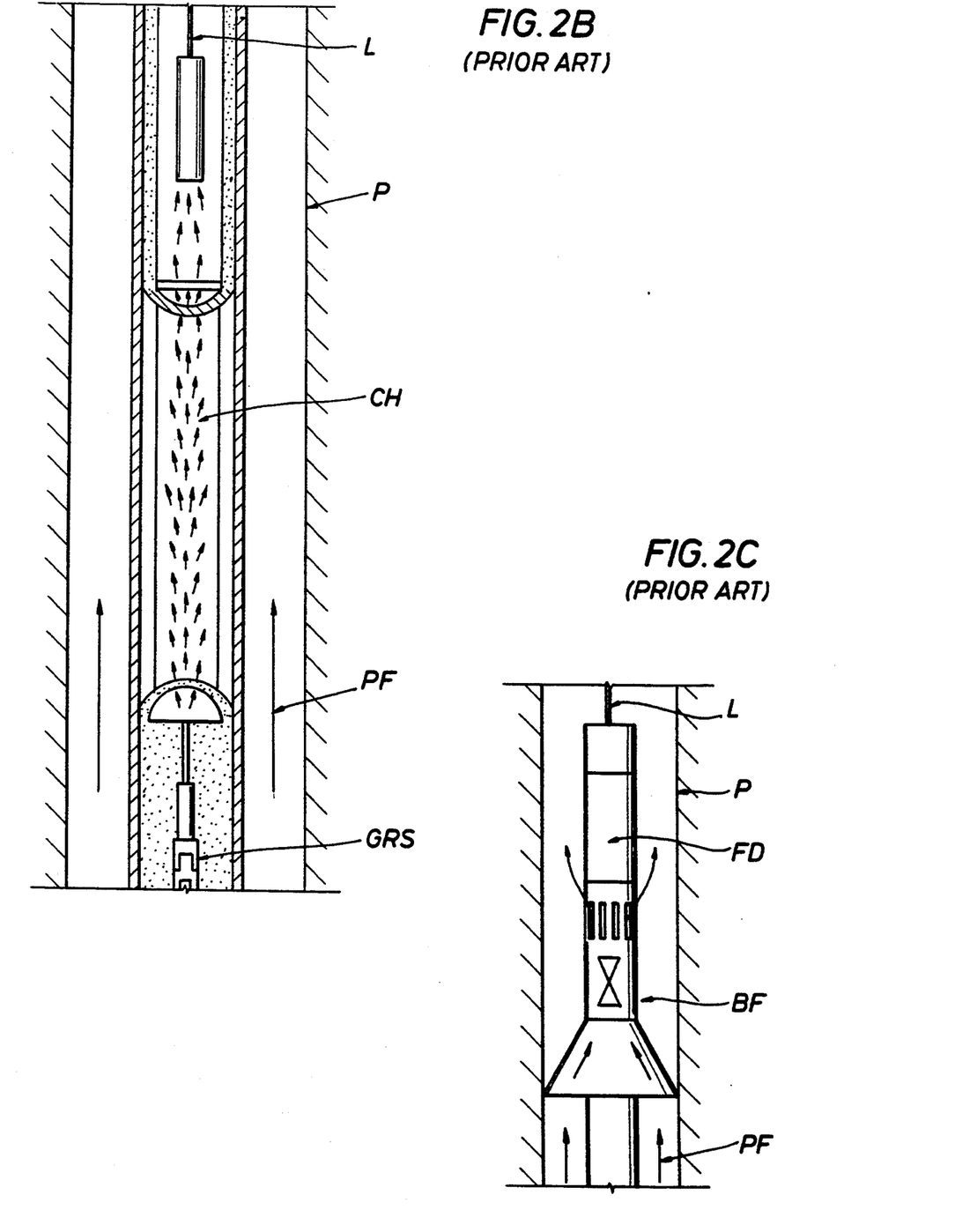
FIG. 2B illustrates a focused density tool.
FIG. 2C illustrates the combined instruments within a pipe.

A schematic of the second instrument, a focused density tool FD, is shown in FIG. 2B. A source GRS on one side of a sampling channel emits gamma radiation. The radiation crosses the sampling channel CH, where the gas and liquid are present. On the other side of the sampling channel, the intensity of the gamma radiation is measured by a counter, and the count rate is converted to a frequency. Increasing the density of the gas/liquid combination in the sampling channel decreases the frequency. Decreasing the density increases the frequency. At the surface, the frequency is converted to a corresponding density of the gas/liquid combination in g/cm$^3$, which is recorded.

The density tool of the preferred embodiment is arranged so that the gamma radiation paths are parallel to the tool housing; in other words, the radiation paths are "focused". For this reason, the tool measures the density of fluid that is near its centerline. The focused density tool is non-diverting, i.e., centralized, allowing passage of the well fluids PF between the tool and the inside pipe wall (or between the tool and the surface of the borehole).

Both the diverting flow meter and the nondiverting, focused density tool are known in the art. Such measuring instruments might be purchased from Computalog, for instance, of Ft. Worth, Tex.

The combination of the diverting flowmeter BF and a focused density instrument FD in a pipe P is shown in FIG. 2C. The diverting flowmeter BF is below the density instrument FD which is centralized and positioned just above the flowmeter discharge. In deviated pipe, gas tends to segregate from the liquid and move along the upper part of the pipe, while the liquid moves along the bottom. The tendency of the gas to segregate from the liquid depends on the pipe size, total flow rate, and deviation angle. Factors promoting segregation, either individually or in combination, are increasing pipe size, decreasing total flow rate, and increasing deviation angle. If the gas were to segregate and move along the upper part of the pipe, it could escape detection by the focused density instrument, since it responds to fluid near its centerline. Should this happen, the density instrument would be unresponsive to the water cut, in which case the density log data would not be useful for profiling. The diverting flowmeter is advantageous in deviated pipe because it mixes gas and liquid and reduces the tendency of the gas to separate from the liquid as the gas/liquid flow moves past the focused density instrument. This helps preserve the utility of the density data for profiling at times when flow conditions favor segregation.

Figure 3:
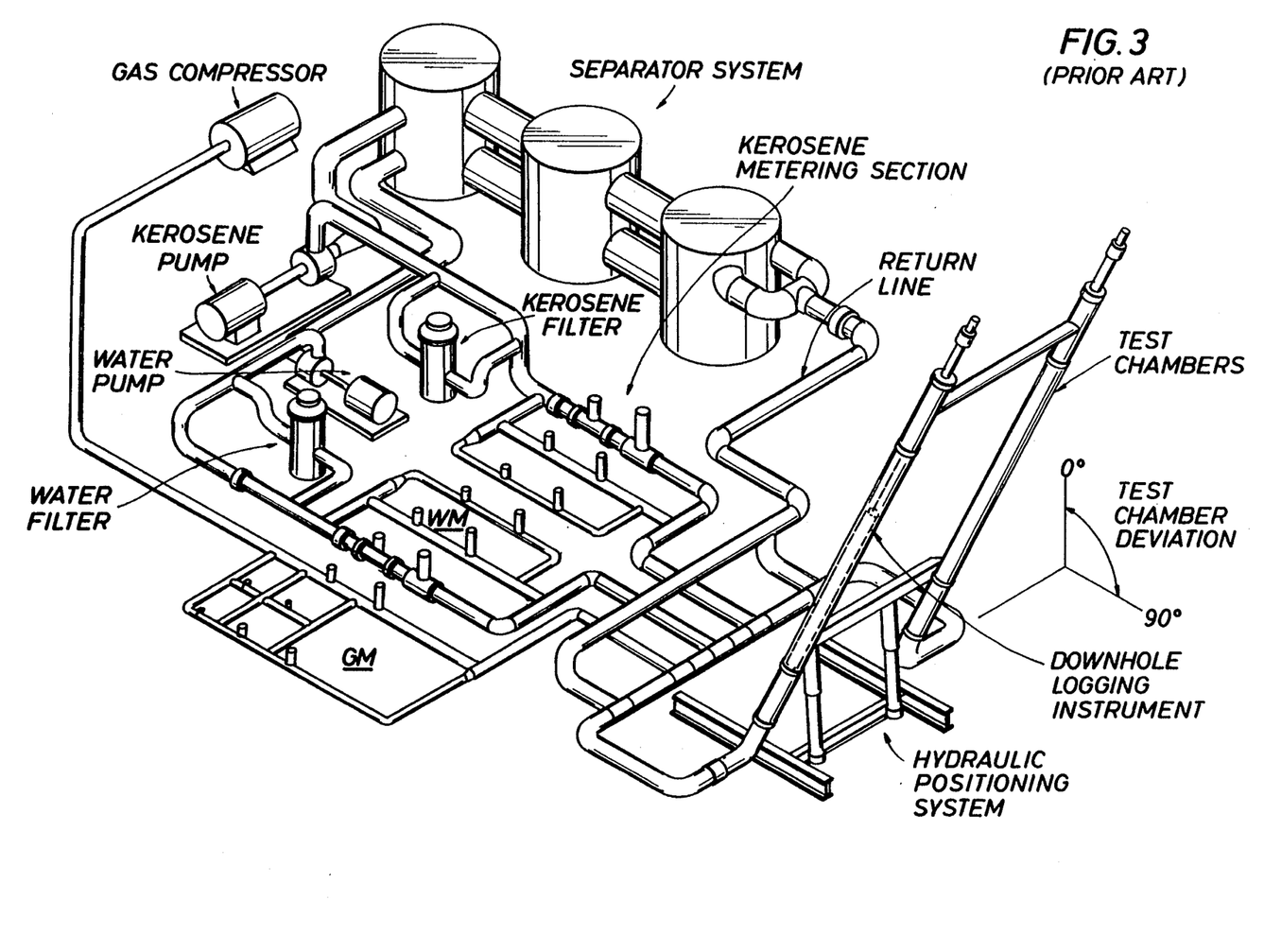
FIG. 3 illustrates typical flow loop test equipment, showing the provision of pipe for containing the measuring instruments of FIG. 2 and means for varying water flow rate and air flow rate.

The logging combination of the diverting flowmeter BF and the focused density tool FD may be "calibrated" in flow loop test equipment. FIG. 3 illustrates typical flow loop test equipment. The calibration data of FIGS. 4A–4C were determined in similar surface test equipment in the following manner. With the combination of instruments situated in a 2.5-in.-ID vertical pipe (at a 0° deviation), air-water flows at various total fluid flow rates and "water cuts" were passed through the pipe while the responses of the logging instruments were recorded. Water flow rate was controlled by water metering section WM. Gas (air) flow rates were controlled by gas metering section GM. The gas comprised air at 70 psi pressure from an air pump and near ambient temperature. Water was used from the municipal supply.

Figure 4A:
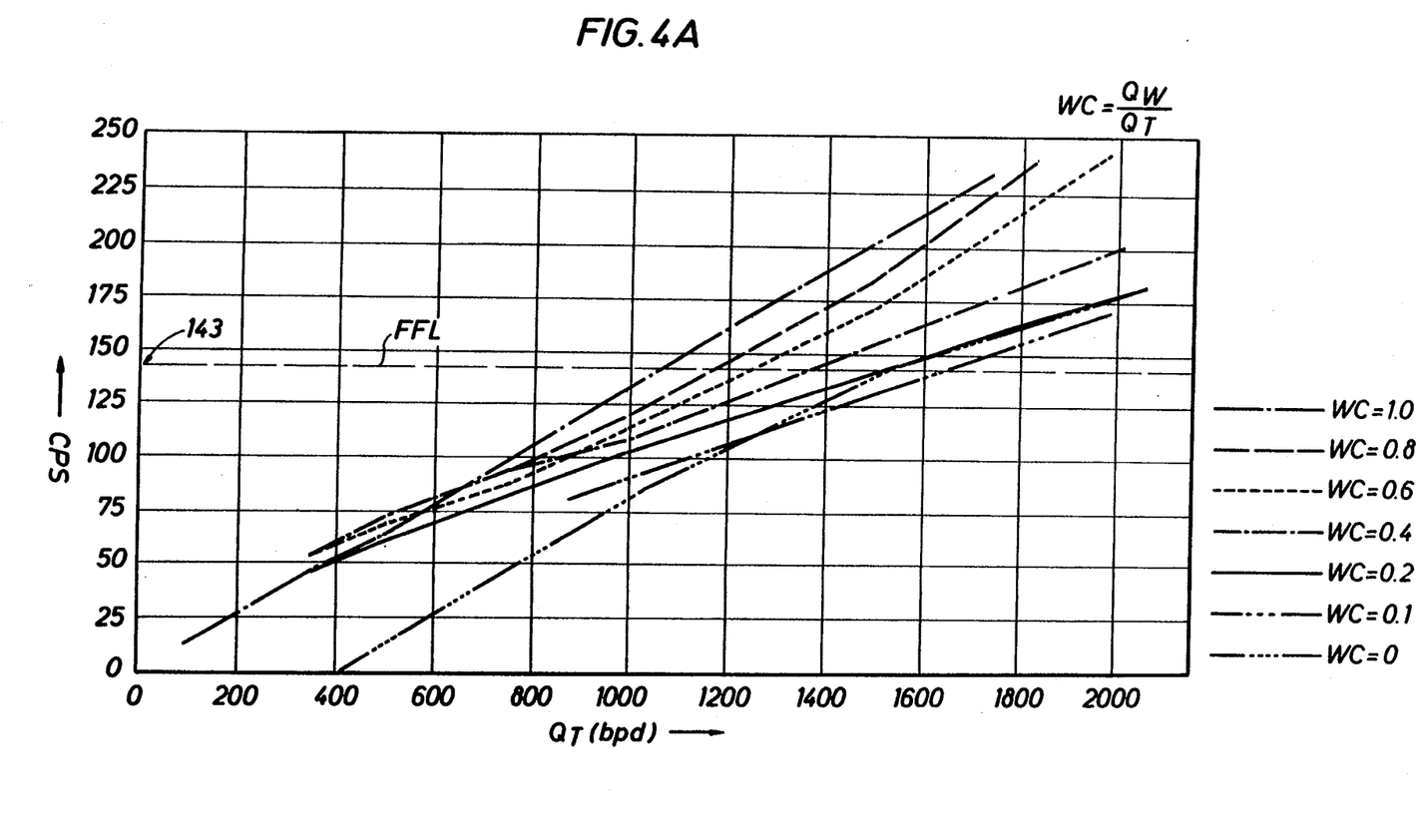
FIG. 4A illustrates calibration data curves wherein the Y axis registers values of a function of fluid flow rate.

FIG. 4A shows the "characterization" of the diverting flowmeter BF, with the rotation rate of the spinner (in CPS) presented on the vertical axis and the total fluid flow rate of gas and water on the horizontal axis (in BPD). The plotted points (symbol "x") represent data recorded during flow loop tests. Various curves, called "response curves", are shown, each one pertaining to a specific value of "water cut" (WC).

Even at a controlled total fluid flow rate and "water cut" in flow loop test equipment, the response of the diverting flowmeter BF fluctuates in gas-water flow, necessitating that the flowmeter response be time-averaged. For any point marked by "x" on the figure, the flowmeter response was time-averaged for a period of 10 minutes. The 10 minute time average is shown.

Figure 4B:
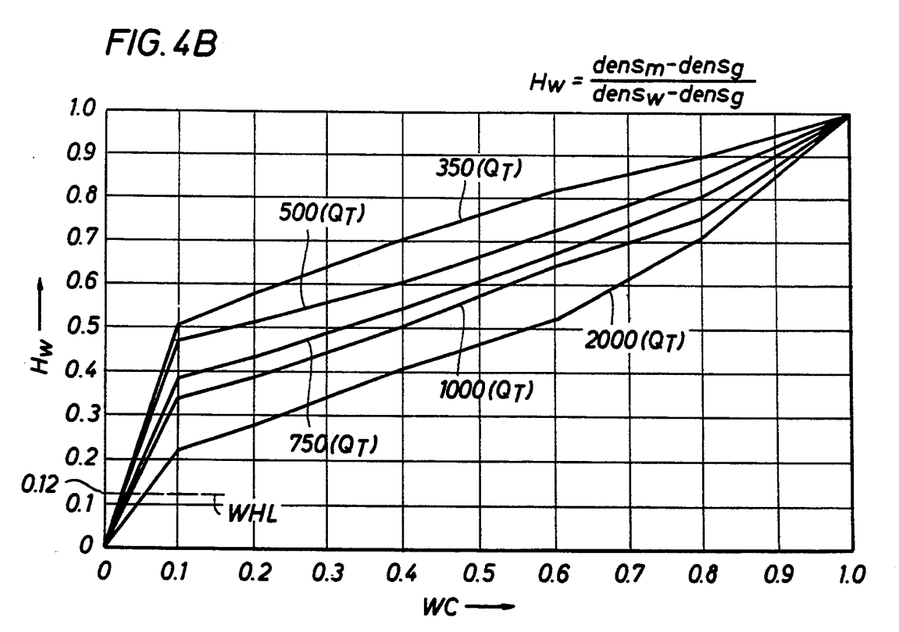
FIG. 4B illustrates calibration data curves wherein the Y axis registers values for a function of fluid density.

FIG. 4B shows the characterization of the focused density instrument FD, with the various "water holdup", $H_w$, values presented on the vertical axis. The horizontal axis presents the "water cut". "Water holdup" is derived from the measured response of the focused density instrument to a gas/liquid flow ($\rho_m$) combined with a value for the density of the liquid, or water ($\rho_w$), and a value for the density of gas ($\rho_g$):

$$H_w = \frac{\rho_m - \rho_g}{\rho_w - \rho_g}$$

For the characterizations of FIG. 4B on the surface test equipment values for $\rho_w$ and $\rho_g$ were measured, where $\rho$=density, g/cm³. The plotted points (symbol "x") represent data collected during the flow loop tests.

In the gas-water flows used in the flow loop tests, the measured density ($\rho_m$) fluctuates, even though the total fluid flow rate and the "water cut" are set to be constant by the test equipment. This necessitates time-averaging the density response. For any point marked by "x" on the figure, the density response was time-averaged for 10 minutes. The value of $H_w$ based on the 10 minute time average of $\rho_m$ is shown.

Figure 4C:
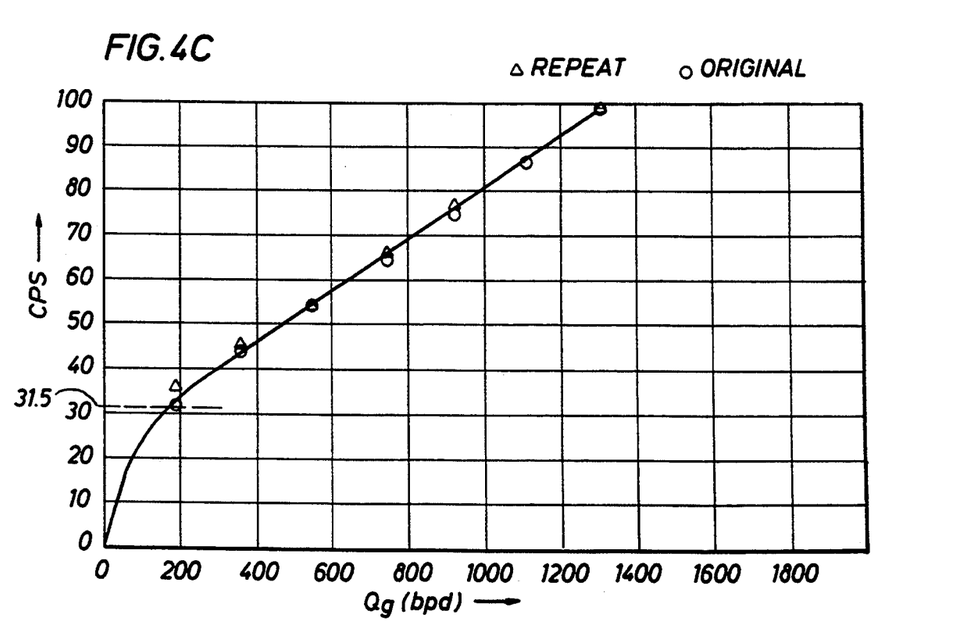
FIG. 4C illustrates a calibration curve appropriate for gas percolating through stagnant water.

FIG. 4C characterizes the diverting flow meter BF in the special single phase production scenario where gas percolates through stagnant water. In this case the X axis measures the flow rate of gas in barrels per day, rather than the total fluid flow rate, since the liquid or water, by definition, is not flowing.

The interpretive method applied to downhole measurements, as taught by the present invention, uses non-in situ calibration data, such as developed above on surface flow loop equipment and shown in FIGS. 4A–4C, to predict a percent of flow of liquid and gas at various downhole depths. The prediction, or profiling, of the preferred embodiment is based upon downhole measured CPS values from a diverting flowmeter and a computed value of $H_w$ based on measured density responses. It is further based upon determined values for the downhole liquid and gas densities. The downhole measured CPS and density values preferably comprise at least eight minute time averages, and may run to 15 minutes or longer time averages. Time averaging stationary downhole instrument readings over such long periods is unusual to the practice of well profiling. It comprises a significant aspect of the present invention. It is taught that, under the circumstances of the present invention, such time averaging significantly increases the sensitivity and accuracy of the gas and liquid profile results.

Predicted flow rates of gas and liquid can be computed from values of total flow rate and water cut, as explained below. From these flow rates, percent contributions can be calculated.

FIGS. 5A–5D and 6A–6D illustrate calculations leading to the quantitative profiling of a particular combined gas/liquid (predominately water) producing well according to the present invention. In the calculation, the calibration data of FIGS. 4A–4C were utilized.

As can be seen from FIGS. 5A–5D, the small circles to the left of the vertical bar of the running temperature and density log, to the right in the figures, indicate that the well contained nine production intervals. The numbers listed between the temperature and density log on the right indicate averaged readings from a diverting flow meter and a focused density tool, taken at nine depths. (Two sets of readings were taken at the lowest depth.) The percent contribution log on the left was compiled according to the teachings of the present invention.

In the example of FIGS. 5A–5D, the measurements for the diverting flow meter were stationary averages over ten minutes. The measurements for the focused density tool were stationary averages over 15 minutes. These times were selected as they appeared to average out the fluctuations in the measurements to a level commensurate with the accuracy obtainable by the method.

The running temperature and density log is presented for two reasons. First, review of the temperature and density log by one of skill in the art provides a quick "qualitative" means to predict that below approximately X,260 feet gas is percolating through a column of stagnant water. Secondly, the "quantitative" gas/liquid well profile log shown on the left hand graph of FIGS. 5, compiled according to the present invention, can be independently corroborated qualitatively, at least to the extent of the accuracy of the qualitative method, by expert reading of the temperature and density log contained in the right hand graph.

Figure 5A:
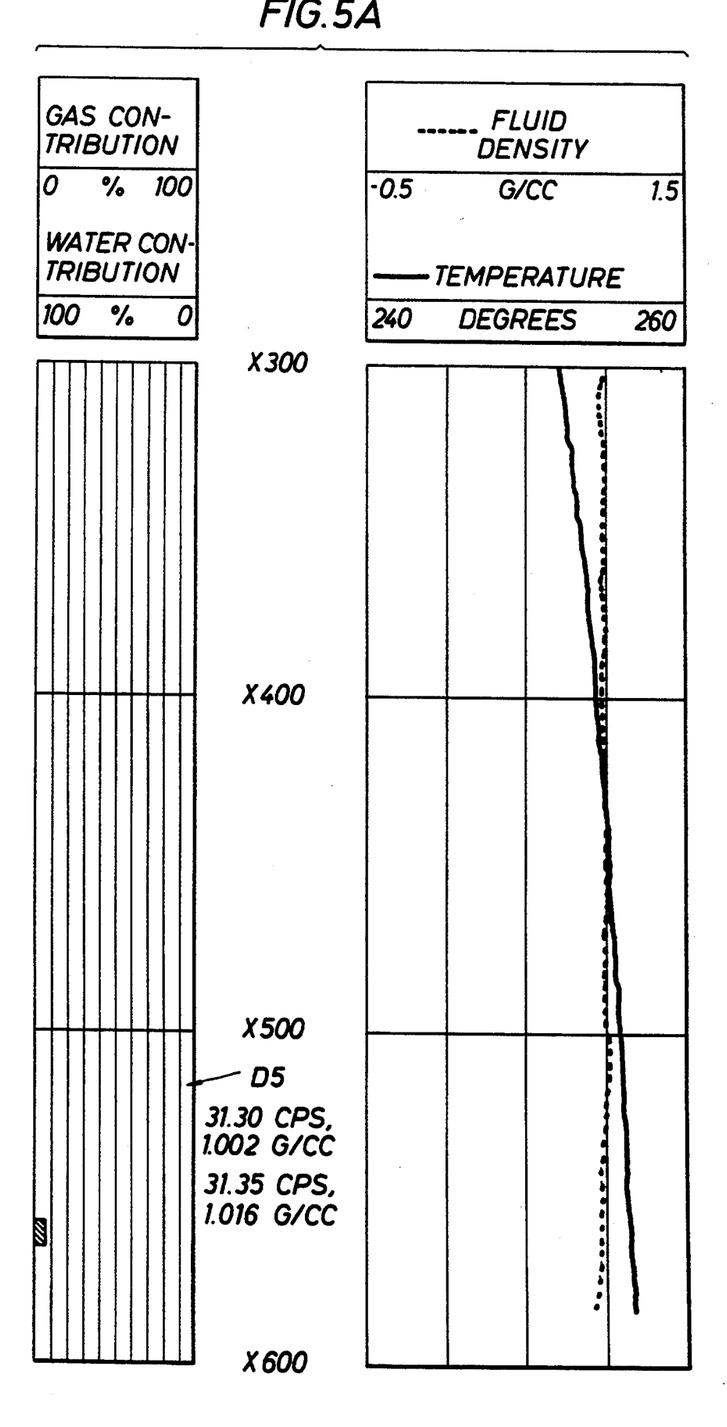
FIGS. 5A–5D illustrate a downhole log of a combined gas/liquid producing well containing a plurality of production intervals.
Figure 5B:
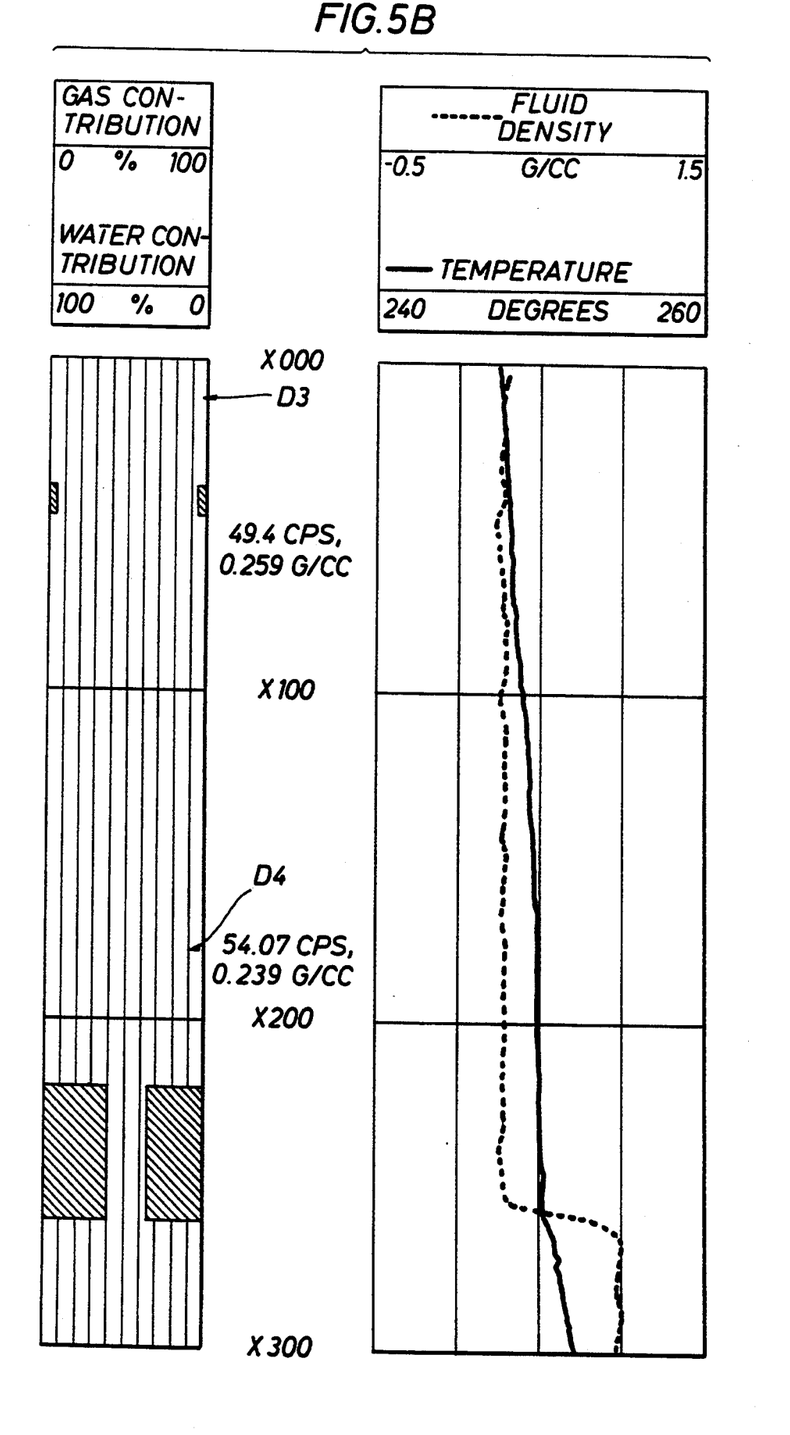
Figure 5C:
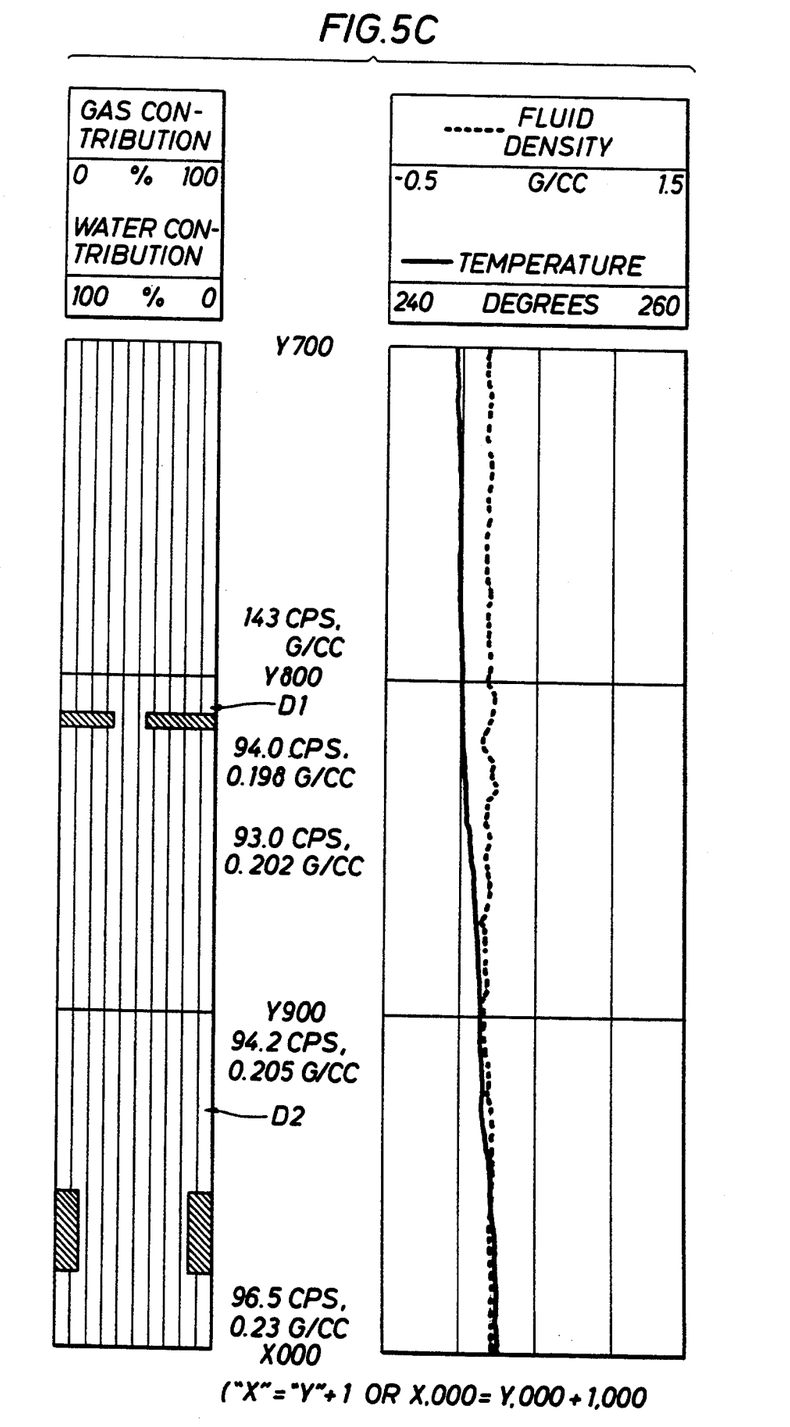
Figure 5D:
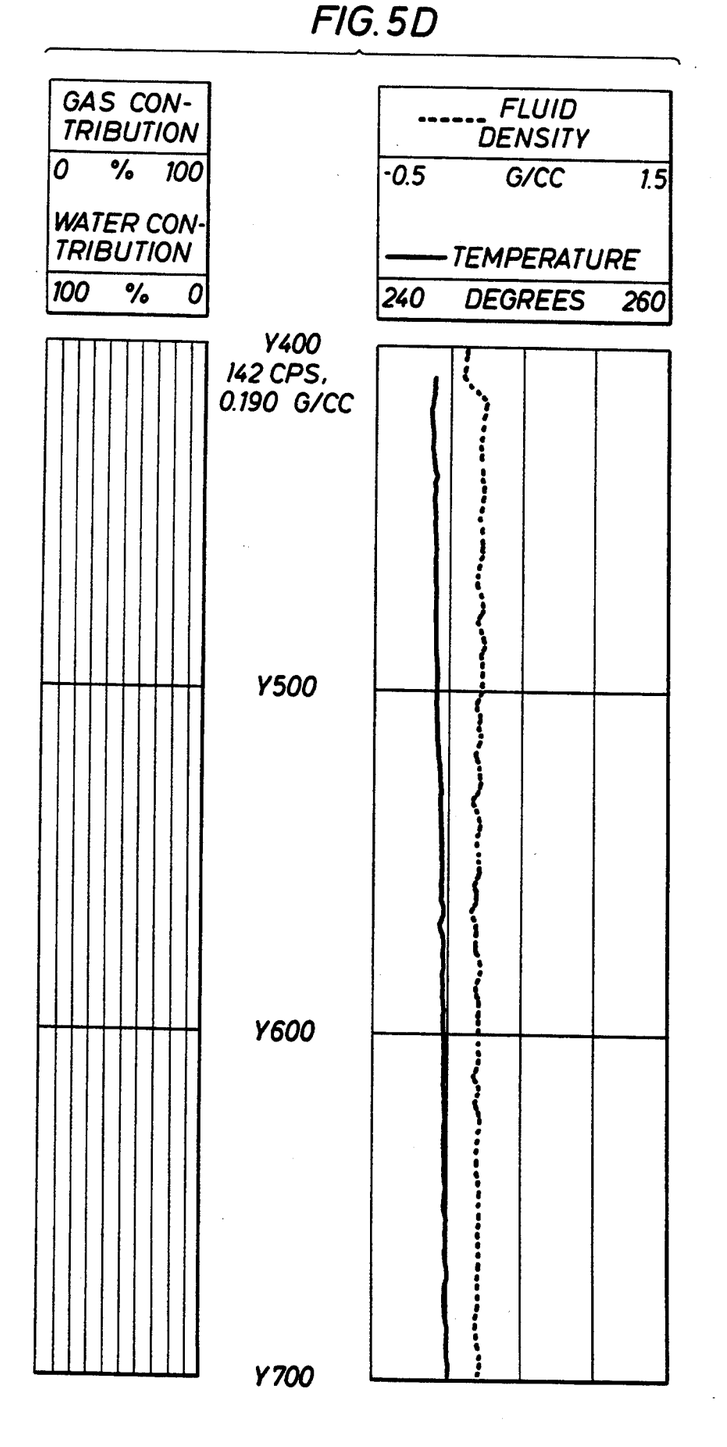

To consider the instrument measurements, moving down the well, FIGS. 5A–5D must be considered in reverse order. The averaged diverting flow meter readings (142 cps) and the focused density tool readings (0.190 g/cc) at approximately Y,400 feet (FIG. 5D) are essentially the same as the averaged readings (143 cps and 0.199 g/cc) at approximately Y,800 feet (FIG. 5C). Hence, it is predicted that neither gas nor liquid is significantly produced by the production interval located at approximately Y,480 feet.

Depth $D_1$ of FIG. 5C illustrates a depth of approximately Y,822 feet. Depth $D_1$ was selected as a depth above all significant production zones. This depth became the so-called uppermost normalizing depth.

Figure 6A:
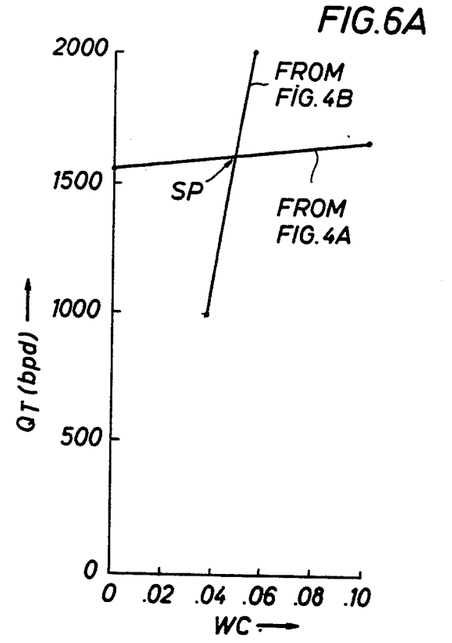
FIGS. 6A–6D illustrate computations for five depths of the well of FIGS. 5, in accordance with the present invention.

FIG. 6A illustrates the computations performed according to the interpretive method of the present invention at depth $D_1$. An averaged value density tool reading of 0.199 grams per cubic cm. is converted to a water holdup reading of 0.12. The water holdup computation involves utilizing a value for the downhole density of the liquid of 1.06 g/cc (essentially water) and a value for the downhole density of the gas of 0.083 g/cc. These two downhole densities were determined prior to the logging by shutting in the well. Other means in the art are known and could be utilized to value the downhole density of the liquid and the gas.

Utilizing the characterizations of FIG. 4B as calibration data, a water holdup line representing 0.12 was extended across the FIG. 4B set of calibration curves. This line is illustrated by dashed line WHL in FIG. 4B. (In practice, the relevant area of FIG. 4B would be enlarged in order to increase the accuracy of determining the intersection points.) Relevant intersection points of the 0.12 water holdup line WHL with the calibration curves is listed in FIG. 6A, showing a series of five "water cut" points correlating with a corresponding set of five total fluid flow rate points. These coordinates define what is referred as a second solution curve.

Likewise, the average measured counts per second reading of 143 at depth Y,822 is extended as a line across FIG. 4A. That line for this depth is shown as dashed line FFL on FIG. 4A. The intersection points of the 143 CPS line FFL with the relevant set of calibration curves on FIG. 4A is indicated in FIG. 6A. Two values of water cut are correlated with two values of total flow rate. These coordinates define what is referred to as a first solution curve.

FIG. 6A illustrates an interpretive graph wherein the two solution curves are plotted. The intersection of the two solution curves yields a solution point SP of water cut = 0.048 and total flow rate = 1600 bpd. If total flow rate equaled 1600 barrels per day with a water cut of 0.048, then 77 barrels per day of liquid (essentially water) would be produced with the remainder of the flow, 1523 barrels per day, being produced as gas. (The percent of liquid flow at the uppermost normalizing depth is 100%, as is the percent of gas flow.) The calculations involved are illustrated below.

$D_1$ — Depth: Y822 (uppermost normalizing depth)

Average Flow Meter - 143 CPS
Readings: Density Meter - .199 G/CC $\rightarrow$ $$H_w = \frac{.199 - .083}{1.06 - .083} = .12$$

| | WC | $Q_t$ | |
|---|---|---|---|
| $H_w = .12 \rightarrow$ | .022 | 350 | |
| | .025 | 500 | |
| | .031 | 750 | from FIG. 4B |
| | .037 | 1,000 | |
| | .055 | 2,000 | |

| | WC | $Q_t$ | |
|---|---|---|---|
| CPS = 143 $\rightarrow$ | .1 | 1,660 | from FIG. 4A |
| | 0 | 1,550 | |

-continued

Solution point
WC = .048
$Q_t$ = 1600 $\rightarrow$ 77 BPD liquid and 1,523 BPD gas Percent of water flow    100%
Percent of gas flow    100%

Downhole density of liquid = 1.06 G/CC
Downhole density of gas = .083 G/CC
Well produces: - 70 BPD liquid
              - 1,500,000 ft³/D gas 1,500,000 ft³/D gas at surface ≈ −2,000 BPD at 4,800 ft It might be noted at this point that the well in fact was known to produce 70 barrels per day of liquid (predominately water) at the surface, and approximately 1½ million cubic feet per day of gas. It is generally considered extremely difficult in the industry to make any prediction as to the production rates for liquid in a combined gas/liquid well where so little liquid is produced in respect to the gas.

The next depth of interest in the example well is depth $D_2$ at Y,930 feet, shown on FIG. 5C. This is so because there is essentially no difference between the averaged counts per second diverting flow meter readings (94.0, 93.0 and 94.2) and the averaged grams per cubic centimeter focused density tool readings (0.198, 0.202, and 0.208) above and below the potential production intervals located at approximately Y,830 and Y,890 feet. Hence, the interpretive method of the present invention predicts no significant production from those intervals.

Figure 6B:
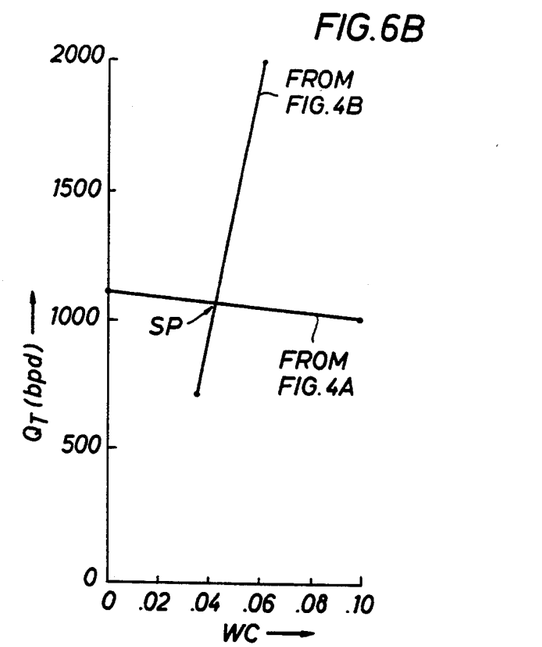

Computations for depth $D_2$ selected at Y,930 feet are illustrated in FIG. 6B and below. At such depth the averaged diverting flow meter reading was 94.2 counts per second and the averaged focused density tool reading was 0.208 grams per cubic cm. A density tool reading of 0.208 grams per cubic cm., given the value for the downhole density of the liquid and gas of the example well, converts to a "water holdup" value of 0.13. Lining the water holdup estimate across the graph of FIG. 4B (not shown), three relevant correlative values of water cut (WC) and total flow rate (QT) were determined from the set of calibration curves. Likewise, drawing the line representing the counts per second of 94.2 across the curves of FIG. 4A (not shown), two relevant water cut and total flow rate values were determined. The set of intersection values from FIG. 4B yielded what is referred to as a second solution curve in the interpretive graph of FIG. 6B, and the set of intersection values from FIG. 4A yielded a what is referred to as a first solution curve in the graph of FIG. 6B. The two solution curves produced a solution point having a water cut value of 0.041 and a total flow rate of 1080 bpd. Such water cut and total flow rate translate into a predicted production of 44 barrels per day of liquid and 1036 barrels per day of gas. Taking the "predicted" liquid flowing at level $D_2$ of 44 barrels per day, and dividing it by the "predicted" liquid flowing at the uppermost normalizing depth $D_1$ of 77 barrels per day, yields the prediction that 57 percent of the liquid is flowing at depth $D_2$. From this prediction one can infer that, therefore, 43 percent of the liquid is being produced by the production interval located at approximately Y,820 feet, between depths $D_1$ and $D_2$. This percent of production of liquid is illustrated by the quantitative gas/liquid well profile to the left of FIG. 5C. Likewise the "predicted" flow rate of 1036 barrels per day of gas at depth $D_2$, out of a total of 1532 barrels per day of gas "predicted" to be flowing at the uppermost normalizing depth $D_1$, results in the prediction of 68 percent of the gas flowing at depth $D_2$. From this one can infer that 32 percent of the gas is produced in the production interval between depths $D_1$ and $D_2$, also illustrated on the gas/liquid well profile log to the left of FIG. 5C. A summary of the calculations associated with FIG. 6B is as follows:

$D_2$ — Depth: Y930

Average Flow Meter - 94.2 CPS
Readings: Density Meter - .208 G/CC $\longrightarrow$ $$H_w = \frac{.208 - .083}{1.06 - .083} = .13$$

$H_w = .13 \longrightarrow$ 
| WC | $Q_t$ |
|---|---|
| .06 | 2000 |
| .04 | 1000 |
| .035 | 750 | from FIG. 4B

CPS = 94.2 $\longrightarrow$
| WC | $Q_t$ |
|---|---|
| 0 | 1120 |
| .1 | 1040 | from FIG. 4A

Figure 6C:
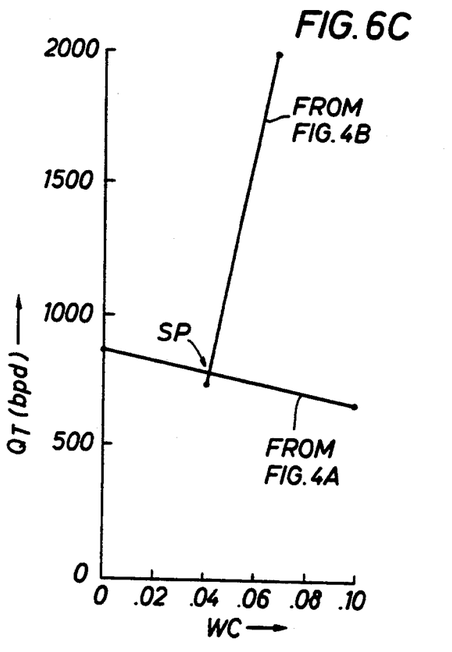

Solution point
WC = .041
$Q_t$ = 1080
$\longrightarrow$ 44 BPD liquid
1036 BPD gas Percent of liquid flow $= \frac{44}{77} = 57\%$ Percent of gas flow $= \frac{1036}{1532} = 68\%$ FIG. 6C and the below calculations illustrate the computations that are performed at depth $D_3$ as illustrated on FIGS. 5C and 5B. Depth $D_3$ lies at approximately X,010 feet. (The readings for depth $D_3$ are shown on the bottom of FIG. 5C.) The average measurement of the diverting flow meter is 66.5 cps. The average reading of the focused density tool is 0.23 grams per cubic cm. A 0.23 grams per cubic cm. measured density translates into a water holdup of 0.15. Drawing the line representing a water holdup of 0.15 across the set of calibration curves of FIG. 4B (again not shown) yields the intersection points listed, and the line of the interpretive graph illustrated, on FIG. 6C. Likewise, drawing the line representing CPS=66.5 across the calibration curves of FIG. 4A (not shown) yields the set of points listed, and the line illustrated in the interpretive graph of FIG. 6C. The intersection of the two solution curves in the interpretive graph represents a solution point, predicting a water cut of 0.04 and a total flow rate of 790 barrels per day. This translates into a "predicted" flow of 32 barrels per day of liquid and 758 barrels per day of gas. Computing the fraction wherein the predicted barrels per day flow of liquid is divided by the predicted barrels per day flow of liquid at the uppermost normalizing depth yields the prediction that 41 percent of the liquid is flowing at depth $D_3$. Likewise, computing the fraction of the predicted barrels per day gas flowing at depth $D_3$ divided by the predicted barrels per day gas flowing at the uppermost normalizing depth produces the prediction that 50% of the gas is flowing at depth $D_3$. If 50% of the gas is flowing at depth $D_3$ and 68% of the gas is flowing at depth $D_2$ above it, then approximately 18% of the gas is being produced in the production interval located at approximately Y,980 feet between depths $D_2$ and $D_3$. Similarly, if 41% of the liquid is flowing at depth $D_3$ and 57% of the liquid is flowing depth $D_2$ above it, then approximately 16% of the liquid should be produced at the production interval located at approximately Y,980 feet between depths $D_2$ and $D_3$. These estimates are reflected in the gas/liquid well profile to the left of FIG. 5C. The computations associated with the graph of FIG. 6C are as follows:

$D_3$ — Depth: X010

Average Flow Meter - 66.5
Readings: Density Meter - .23 $\longrightarrow H_w = \frac{.23 - .083}{1.06 - .083} = .15$ $H_w = .15 \longrightarrow$
| WC | $Q_t$ |
|---|---|
| .07 | 2000 |
| .045 | 1000 |
| .04 | 750 | from FIG. 4B

CPS = 66.5 $\longrightarrow$
| WC | $Q_t$ |
|---|---|
| 0 | 880 |
| .1 | 680 | from FIG. 4A

Solution point
WC = .04
$Q_t$ = 790
$\longrightarrow$ 32 BPD liquid
758 BPD gas

Percent of liquid flow $= \frac{32}{77} = 41\%$

Percent of gas flow $= \frac{758}{1523} = 50\%$

Depth $D_4$ of X,180 feet is illustrated on FIG. 5B. There being no significant change between the readings at a depth of approximately X,060 feet (49.4 CPS and 0.259 g/cc) and of X,180 feet (54.07 CPS and 0.239 g/cc), it is predicted that little or no production is coming from the production interval located at approximately X,130 feet. In fact, averaging the readings over the time periods taught above yields sufficiently sensitive and accurate data as to permit a prediction of minor "theifing" by the production interval located at approximately X,130 feet. This "theifing" is in the order of 2% to 3% of total production. The ability to predict "theifing" in the order of 2% to 3% is remarkable and of definite economic impact to the well owner. Further, it highlights the unexpected sensitivity and accuracy of the present method to quantitatively profile gas/liquid production.

Figure 6D:
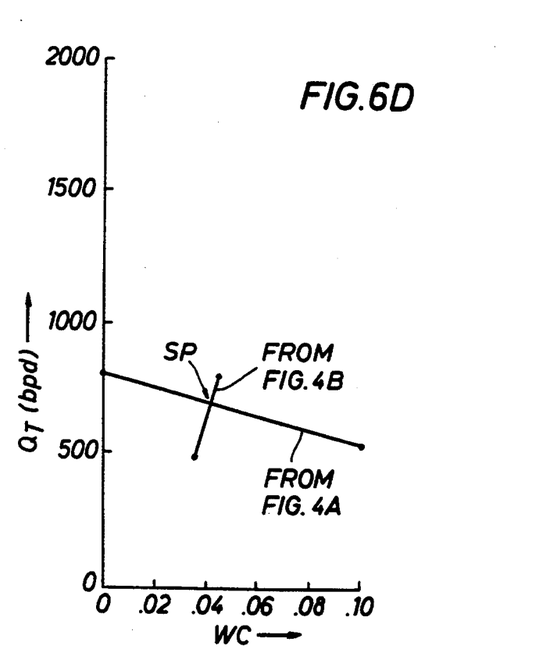

Similar computations as to the above were computed for depth $D_4$, and are reflected on FIG. 6D. These computations resulted in a prediction of 36% of the liquid flow flowing at depth $D_4$ and 45% of the gas flow flowing at depth $D_4$. Comparing the predicted percent flow past depth $D_4$ with the predicted percent flow past depth $D_3$, it is predicted that approximately 5% of the gas and 5% of the liquid is being produced at the production interval located between the two depths $D_3$ and $D_4$, or at approximately X,040 feet. This percent is reflected in the gas/liquid well profile to the left of FIG. 5B. The calculations associated with FIG. 6D are as follows:

D — Depth: X180

-continued

Average Flow Meter - 54 CPS
Readings: Density Meter - .239 G/CC →

$$H_w = \frac{.239 - .083}{1.06 - .083} = .16$$

$H_w = .16$ →

| WC | $Q_t$ |
|---|---|
| .03 | 350 |
| .035 | 500 |
| .042 | 750 |
| .05 | 1,000 |
| .075 | 2,000 | from FIG. 4B

CPS = 54 →

| WC | $Q_t$ |
|---|---|
| .1 | 560 |
| 0 | 810 | from FIG. 4A

Solution point
WC = .04
$Q_t = 710$ → 28 BPD liquid 682 BPD gas

Percent of water flow - 36%
Percent of gas flow - 45%

Review of the running temperature and density logs, presented as the graphs to the right in FIG. 5, suggest to one skilled in the art that a column of stagnant water exists below the production level located at approximately X,240 feet (FIG. 5B). Hence, all liquid flowing at depth $D_4$, or approximately 36%, should be produced by the production interval located at approximately X,240. The averaged measured instrument readings of approximately 31.5 cps and 1.01 grams per cubic cm. (an average itself in this historical example of two sets of readings) themselves independently suggest that gas is percolating at level $D_5$, on FIG. 5A, located at approximately X,550 feet, through a column of stagnant water. FIG. 6E, interpolating from FIG. 4C containing calibration data for percolating gas, suggests that the quantity of gas passing depth $D_5$ is 160 barrels per day or approximately 10% of the predicted production at the uppermost normalizing level. However, in actual fact, the readings at level $D_5$ varied, as mentioned above. A second set of readings revealed no counts per second at all at level $D_5$. Hence, for the gas/liquid well profile of the example presented, the 10% figure was halved to 5%, as illustrated in the gas/liquid well profile to the left of FIG. 5A.

The calculations above predicted that 36% of the liquid flow was flowing at depth $D_4$. Since it is determined that no liquid is flowing at depth $D_5$, all 36% of the liquid is predicted to be produced at the production interval located at X,240 feet between depth $D_4$ and depth $D_5$. Likewise, it was above calculated that 45% of the gas was flowing at depth $D_4$. Assuming that 5% of the gas is flowing at depth $D_5$, 40% of the gas should be produced by the production interval located at X,240 feet. These percents are reflected in the gas/liquid well profile to the left of the graph in FIG. 5C.

There are a variety of means for suspecting that gas is percolating through a column of stagnant water below the production interval located at approximately X,240 feet. For instance, if the cps reading of 31.50 and grams per cubic cm. reading of 1.01 reflected moving liquid, resort to the calibration curves would indicate that significantly more liquid was being produced at level $D_5$ than the known quantity of liquid (approximately 70 barrels per day) being produced at the surface of the well. Hence, the assumption that that liquid is moving at level $D_5$ is inconsistent with known facts. Furthermore, level $D_4$ sees 36% of the total liquid flow or somewhere in the neighborhood of a "predicted" 25 barrels per day. If an amount of liquid similar to 25 barrels per day were moving past depth $D_5$, the gas being produced at depth $D_5$ could not cause the drop in temperature indicated in the running temperature log at that level, as one skilled in the art of reading downhole temperature and density logs would know. Thus, the present method provides independent corroboration for the prediction of a stagnant column of water existing through the first production level at approximately X,560 feet and up to the second production level at approximately X,250 feet. The calculations associated with level $D_5$ are as follows:

$D_5$ — Depth: X550

$D_5$ — gas percolating

Flow Meter - 31.5 CPS
Density Meter - 1.01 G/CC

From FIG 4C   $Q_G = 160$ BPD $$\text{Percent gas} = \frac{160}{1523} = -10\%$$

(But, intermittent)

In the example charted in FIGS. 5A through 5D, the temperature and density log were independently qualitatively read by an expert in the field. The expert's predictions were compared with the gas/liquid well profile predictions graphed to the left in FIGS. 5A through 5D. The expert's predictions corroborated extremely well with the gas/liquid well profiling information of the present invention to the extent of the usefulness of a qualitative method. That is, the expert was able to corroborate the present invention's prediction that the liquid comes in with the major gas production. The expert could not attempt to corroborate the predicted percent of gas and liquid from each production interval since the qualitative method is not capable of making such distinctions. The agreement, to the extent possible, offered an unexpectedly high level of independent corroboration for the accuracy of the present invention.

The above example illustrates that the method of the present invention has the sensitivity to locate a 5% contribution of gas and/or of liquid. This marks a remarkable sensitivity, not heretofore expected from dynamic downhole measuring techniques or static short term time averaging of downhole measurements. It is believed that the longer term averaging taught by the present invention and not found in the industry reduces statistical restraints imposed upon the measurements by levels of fluctuation in the downhole flow regime. The present invention teaches averaging out the fluctuations, improving thereby the sensitivity, the utility, and the economic impact of the method.

The method of the present invention offers sufficient sensitivity that if an interval is not producing at all, the basket flow meter readings stationarily averaged above and below that interval, as taught by the invention, are very close together. The well owner, thus, can distinguish between marginally producing intervals and non-producing intervals. The capacity to identify non-producing intervals in an early well has significant economic impact. The owner can forego considerable expenses involved in completing the corresponding intervals in subsequent nearby wells. Furthermore, if bottom or lower intervals are determined to be marginal producers, the owner can economically balance the costs of the final drilling to reach the lower producing intervals versus their contribution to total well production. As in the example of FIGS. 5A through 5D, drilling and completing the well from X,300 feet to X,600 feet may not justify its cost in order to increase gas production by a mere 5%. Lastly, sensitivity of the present invention to identify "theifing" zones can have economic importance. The cost of the known remedy of a cement squeeze can be balanced against the value of saving an additional 2%-3% of production.

The foregoing disclosure and description of the invention are illustrative and explanatory thereof. Various changes in the size, shape and materials as well as the details of the illustrated construction may be made without departing from the spirit of the invention.

I claim:

1. A method for profiling a gas and liquid producing well having a plurality of production intervals ordered in depth from upper to lower, and producing gas and liquid through a well bore at a known deviation angle, comprising
    creating calibration data from a fluid flow rate instrument and a fluid density instrument within non-in situ test equipment wherein liquid flow rates and gas flow rates are controllably varied;
    estimating downhole gas density and downhole liquid density;
    averaging measurements from the fluid flow rate instrument and the fluid density instrument over a period of time at each of a plurality of downhole depths in the gas and liquid producing well; and
    predicting a percent of total gas flow and a percent of total liquid flow at a downhole depth based on at least the calibration data, the values of downhole densities and the average measurements at the depth, said predictions comprising a part of a well profile.

2. The method of claim 1 that includes converting the measurements from the fluid density measuring instrument to the variable "water holdup".

3. The method of claim 1 wherein the averaging is over a period of at least eight minutes.

4. The method of claim 1 wherein the fluid flow rate and fluid density instrument comprise a diverting flow meter and a focused density tool.

5. The method of claim 1 wherein the plurality of downhole depths includes a depth below all production intervals, a depth between each production interval and an uppermost normalizing depth above all production intervals.

6. The method of claim 1 wherein the creating calibration data includes forming a first set of calibration curves whose Y axis comprises values for a function of fluid flow rate and X axis comprises values for total flow rate and each curve corresponds to a different water cut; and forming a second set of calibration curves whose Y axis comprises values for a function of fluid density and X axis comprises values for water cut, and each curve corresponds to a different total fluid flow rate.

7. The method of claim 6 wherein the predicting includes utilizing an intersection of two solution curves, the first solution curve being defined by the intersection of the first set of calibration curves with a line defining an average measured value of a function of fluid flow rate and the second solution curve being defined by an intersection of the second set of calibration curves with a line defining a value for a function of average measured fluid density.

8. The method of claim 1 wherein the non-in situ test equipment comprises flow loop test equipment.

9. The method of claim 8 wherein the flow loop test equipment includes pipe set at an angle deviated the same as the pipe of the gas and liquid producing well.

10. The method of claim 1 wherein the calibration data includes data from simulating gas percolating through stagnant water.

11. The method of claim 10 that includes logging a measure of downhole temperature and a measure of downhole density and using a qualitative interpretation of the downhole temperature and density log to indicate when to use calibration data for percolating gas.

12. The method of claim 1 wherein the predicting includes dividing a predicted gas flow rate at a depth by a predicted gas flow rate at an uppermost normalizing depth and dividing a predicted liquid flow rate at a depth by a predicted liquid flow rate at an uppermost normalizing depth.

13. The method of claim 1 wherein the valuing downhole gas and liquid density is determined by shutting in the well.

* * * * *